United States Patent
Shaw

(10) Patent No.: US 6,210,371 B1
(45) Date of Patent: Apr. 3, 2001

(54) WINGED I.V. SET

(75) Inventor: Thomas J. Shaw, Little Elm, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 0 days.

(21) Appl. No.: 09/281,537

(22) Filed: Mar. 30, 1999

(51) Int. Cl.[7] ................................................. A61M 5/178
(52) U.S. Cl. ...................... 604/164.08; 604/177; 604/198
(58) Field of Search ..................... 604/162, 163, 604/164, 165, 171, 174, 177, 178, 198, 195, 110, 263

(56) References Cited

U.S. PATENT DOCUMENTS

| | | |
|---|---|---|
| 4,474,831 | 10/1984 | Kulli . |
| 4,820,282 | 4/1989 | Hogan . |
| 4,973,316 * | 11/1990 | Dysarz ................................. 604/195 |
| 5,088,982 | 2/1992 | Ryan . |
| 5,120,320 | 6/1992 | Fayngold . |
| 5,129,884 | 7/1992 | Dysarz . |
| 5,192,275 | 3/1993 | Burns . |
| 5,267,961 | 12/1993 | Shaw . |
| 5,330,438 | 7/1994 | Gollobin et al. . |
| 5,376,075 * | 12/1994 | Haughton et al. ................... 604/158 |
| 5,385,551 | 1/1995 | Shaw . |
| 5,389,076 | 2/1995 | Shaw . |
| 5,407,431 | 4/1995 | Botich et al. . |
| 5,409,461 | 4/1995 | Steinman . |
| 5,423,758 | 6/1995 | Shaw . |
| 5,501,675 | 3/1996 | Erskine . |
| 5,562,629 | 10/1996 | Haughton et al. . |
| 5,562,634 | 10/1996 | Flumene et al. . |
| 5,573,510 | 11/1996 | Isaacson . |
| 5,575,777 | 11/1996 | Cover et al. . |
| 5,578,011 | 11/1996 | Shaw . |
| 5,676,658 | 10/1997 | Erskine . |
| 5,746,215 * | 5/1998 | Manjarrez ............................ 128/763 |
| 5,779,679 * | 7/1998 | Shaw .................................... 604/158 |

* cited by examiner

Primary Examiner—Sharon Kennedy
Assistant Examiner—Catherine Serke
(74) Attorney, Agent, or Firm—Locke Liddell & Sapp LLP

(57) ABSTRACT

A retractable winged I.V. set has a slidable retraction body mounted in a hollow chamber of a housing. The retraction body has a hollow needle fixed in its front end and a tube connector for passing fluid from an external reservoir through the needle. The housing has a pivoting releasable latch preferably configured as dual opposed latches that are biased to normally encroach into the chamber through an opening in the wall of the housing. A catch portion on the retraction body is contacted by an encroaching latch portion to hold the retraction body in an unretracted position with the needle exposed for use. When the latches are released, a spring drives the retraction body to the back of the chamber and withdraws the needle into the housing.

18 Claims, 3 Drawing Sheets

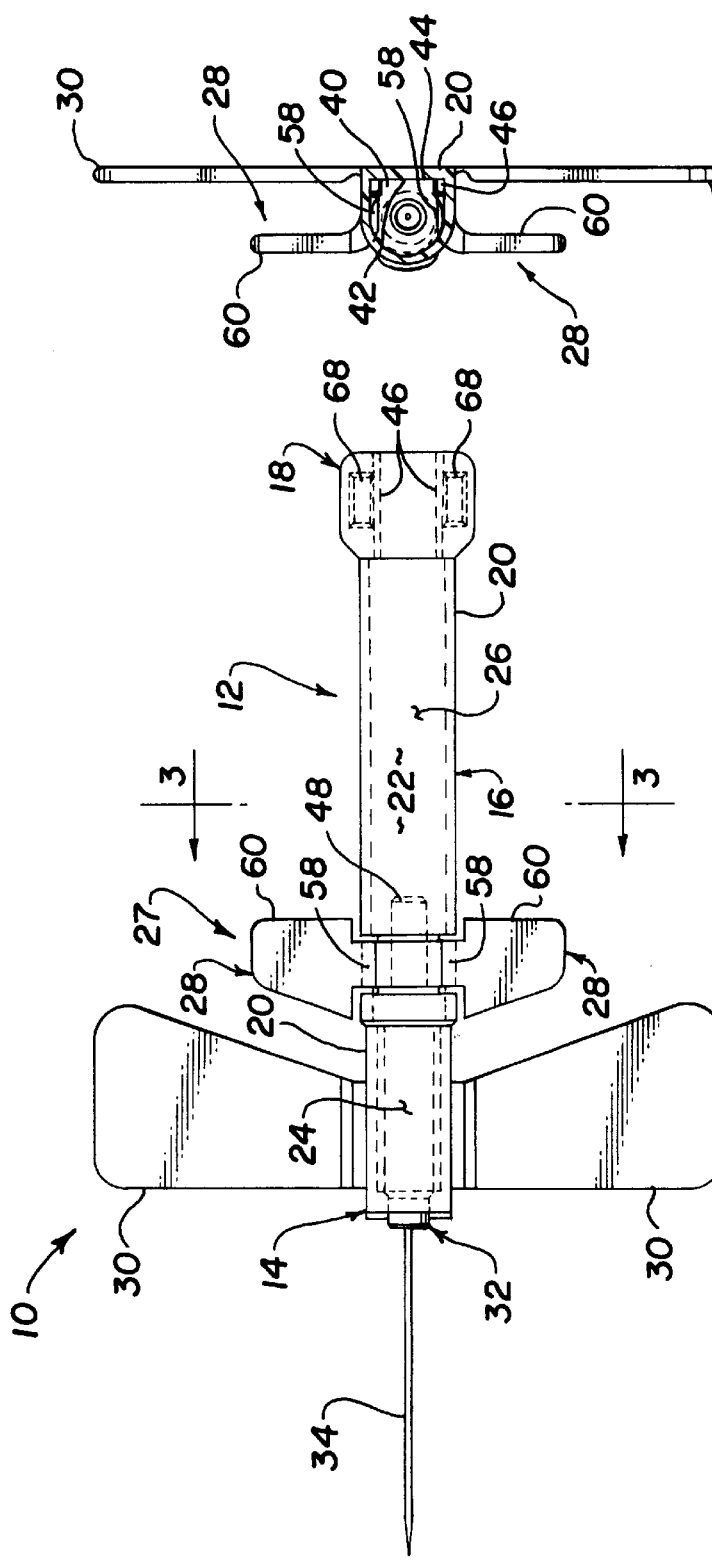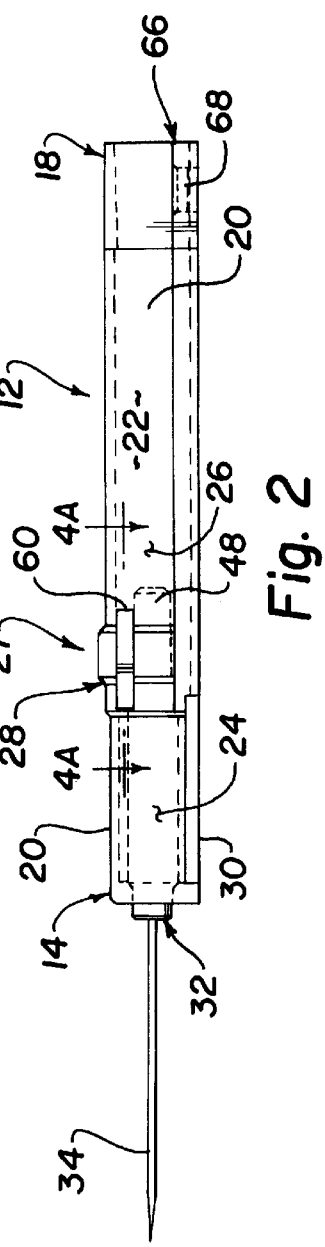

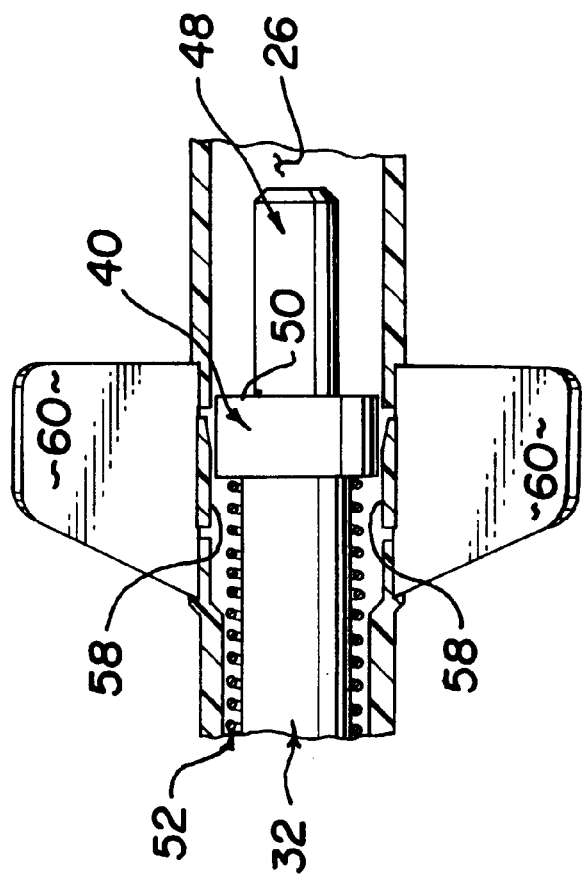
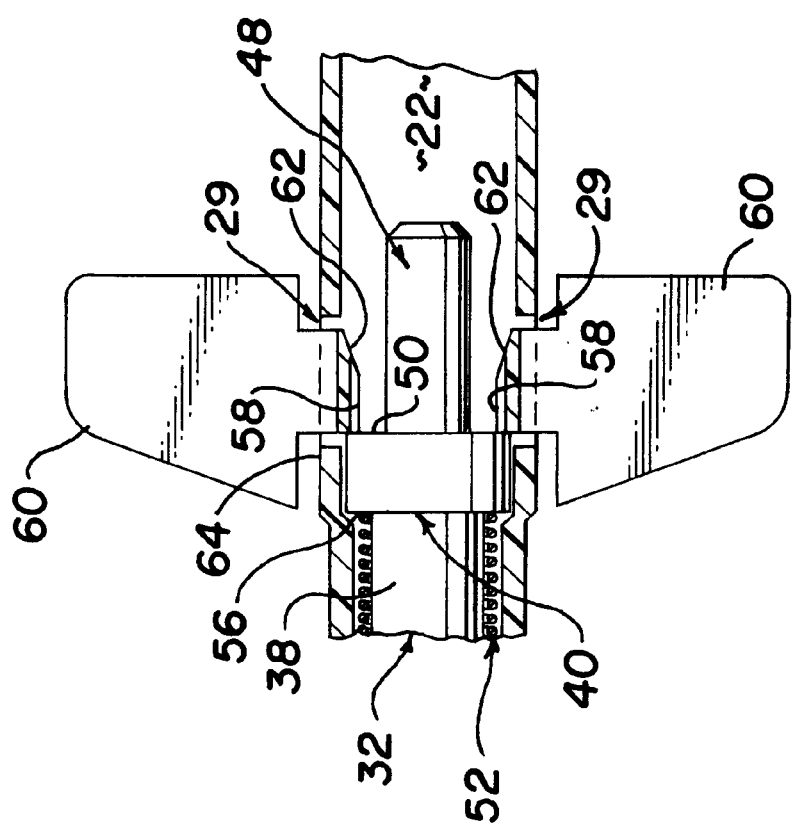

WINGED I.V. SET

FIELD OF THE INVENTION

The invention is a medical device to make a temporary intravenous patient connection.

BACKGROUND OF THE PRIOR ART

I.V. sets are well-known in the art for delivering intravenous fluid to a patient by means of a needle connected through a winged body. They are designed to be temporarily installed to deliver fluid directly to the patient's vein through the extended needle. The wings are used to handle the assembly during insertion and withdrawal and to stabilize the device. The wings provide a broad contact area which allows taping the device to the patient while discouraging movement, especially any rotation, of the device.

A problem occurs upon withdrawal because the needle, now contaminated with blood or other body fluid, must be disposed of without risking needle sticks to medical personnel engaged in the operation of withdrawing the winged I.V. set or to hospital disposal personnel. Caps or covers that are mounted over the needle are not a satisfactory solution because someone must put them in place and because they can become loose and expose a used needle.

U.S. Pat. No. 5,088,932 to Ryan for Safety Winged Needle Medical Devices discloses a double wing IV set in which a slidable hollow winged shield is used to cover a removed needle. One set of wings is attached to a hollow winged shield and one set of wings to a hollow inner tube encircled in part by the hollow winged shield. During use, the shield is frictionally engaged over one end of the inner tube which carries the needle on its other end. When finished, the needle is covered by separately gripping the sets of wings to move the shield forward relative to the inner tube until the shield is locked into position covering the needle.

U.S. Pat. No. 5,120,320 to Fayngold for IV Infusion or Blood Collection Assembly w/Automatic Safety Feature discloses a single wing IV set which uses a separate slidable two-part shield to cover a removed needle/tube assembly. The shield may be opened and positioned around the needle/tube assembly rather than requiring a threading process. Once in place, the needle is covered by pulling the assembly back through the shield which uses guide grooves for the wings to control orientation and to deliver the wings over a ledge into a rear slot which locks the system in its covered position.

U.S. Pat. No. 5,330,438 to Gollobin et al. for Protective Sheath for Butterfly Needles and IV Intusion Set and Sheath Assembly and U.S. Pat. No. 5,192,275 to Burns for IV infusion or Blood Collection Guard Assembly both disclose single wing IV sets which use slidable protective sheaths to cover removed needle/tube assemblies. The sheaths are manually slid over the assembly to cover the needle. Gollobin locks the sheath in the covered position by capturing the wings in a fashion si ar to Payngold (above), while Burns' cover has grooves to allow the wings to travel past but does not appear to positively interact with the wings. The cover in Burns is locked in the extended position by locking lugs on the housing which drop off a ledge into indentations or slots.

U.S. Pat. No. 5,409,461 to Steinman for Catheter Introducer Assembly with Needle Shielding Device discloses a winged catheter introducer in which a needle is used to introduce an IV tube into the patient, and then drawn back manually through the tube and into a holding container for safe storage, leaving a catheter in place to provide fluid communication between the patient and the IV. The wings are not involved in the retraction of the needle.

Prior art safety systems for winged I.V. sets are seen to be problematic. Most of the prior art safety winged I.V. sets rely on manual sliding of a cover over the needle. They almost always involve the need for two handed operation and may not be operated until after the needle is removed and clear of the patient. Some of the systems must be threaded into pre-existing winged I.V. sets creating additional difficulties for healthcare workers prior to insertion of the needle. They also open the possibility for additional error if improperly put in place. Almost all of the systems require healthcare workers to put their hands around and near the exposed needle in order to slide the cover or sheath into place around it. These problems are reduced or eliminated by the present invention.

Additionally, it is important that winged I.V. sets be easily molded on production equipment in large quantities and have few parts. Assembly is equally important because the devices are mass produced and preferably assembled with the aid of machines. The present invention is a significant improvement over the prior art which allows safe, one-handed controlled retraction of the needle directly from the patient without removing the device from its pre-retracted position. The present invention is economical to mass produce and assemble at low cost. The housing can be molded in one piece. The only other part is the retraction body, except for the needle and retraction spring. The present invention offers a significant improvement over the prior art devices and accomplishes all of these objects and more.

SUMMARY OF THE INVENTION

The present invention provides a fully retractable winged I.V. device which is not much larger than a conventional non-retractable device. The main body of the retractable winged I.V. apparatus comprises an elongated housing having a front end, an intermediate portion and a back end. The housing has an elongated wall forming a hollow chamber within the housing extending from the front end to the back end. The hollow chamber may be regarded as divided into a front portion and a rear portion which are separated by a releasable latch preferably comprising a pair of oppositely located releasable latches on either side of the housing.

A needle bearing retraction body is mounted for sliding movement within the chamber. The retraction body is positionable in an unretracted position in the front portion of the chamber with the needle exposed. The needle extends from the front of the retraction body and would normally be provided with a cap over the needle which is removed by the user just prior to use. The retraction body has a catch portion positionable just ahead of the releasable latch to hold the retraction body in the unretracted position. A biasing element in driving contact with the retraction body tends to drive the retraction body into the rear portion of the chamber in response to release of the releasable latch thereby moving the retraction body into a retracted position with the needle protected. That is, the entire needle is drawn back into the elongated housing when the retraction body moves into the retracted position. A back end portion of the retraction body is provided with a tubing connector in fluid communication with the needle and a length of tubing having one end pushed onto the tubing connector. The tubing extends from an opening in the back of the housing with enough clearance between the tubing and the housing to prevent any interference that might occur during movement of the retraction body. In the usual manner, the free end of the tubing is connected to a fluid reservoir usually through a drip control mechanism which is elevated to deliver fluid to the patient through the device.

The housing and retraction body are slidingly moveable, but equipped with cooperating surfaces which maintain the orientation of the retraction body relative to the housing. This prevents the retraction body and the needle fixed therein from rotating relative to the housing. Preferred cooperating surfaces are a flat surface in the floor of the housing and a corresponding flat surface on the retraction body that slides along the flat surface of the in housing. Cooperating surfaces other than at the bottom of the retraction body and the housing are contemplated to maintain angular orientation of the retraction body relative to the housing.

The releasable latch is pivotally mounted in combination with the elongated wall of the housing, for pivotal movement with respect to the housing. The releasable latch comprises at least one encroaching part and at least one projecting part. The encroaching part normally encroaches into the hollow chamber of the housing through an opening in the wall, preferably opposed openings on opposite sides of the elongated housing. The encroaching part is configured to intrude into the hollow chamber behind the catch portion of the retraction body when the retraction body is in the unretracted position. The at least one projecting part is arranged generally in right angle relation to the encroaching part and designed to pivot the encroaching part away from the retraction body thereby releasing the retraction body for movement into the retracted position. The releasable latch preferably comprises dual releasable latches arranged in opposite mirrored relationship to each other on opposite sides of the housing. The projecting parts of the dual latches normally extend generally laterally and are elevated with respect to the housing. The releasable latch or latches are preferably molded to the wall of the housing by means of a living hinge and extend outward from the upper part of the housing.

In order to use the device, the health care provider sterilizes the skin and then removes the cap from the device and engages the needle. The wings on the apparatus are conformed to the patient and taped to hold the device in place on the patient, usually on the arm. Fluid is provided from a reservoir connected to the back end of the rubber tubing which is in fluid contact with the needle through the retraction body.

When there is no further need for delivering intravenous fluid to the patient, a nurse can simply pinch the projecting parts of the releasable catch together between the thumb and finger thereby moving the encroaching parts laterally outwardly from the housing chamber where they no longer restrain the retraction body, which is immediately retracted by the spring. The needle is drawn inside the housing and protected from any further chance of creating a needle stick danger to anyone. The tape is removed from the wings and the device removed from the patient.

Apart from the spring and needle, there are only two parts. The elongated housing body is divided into an upper and lower part along a separation line. It is molded as one part and then folded over to form the hollow chamber and housing. The retraction body is easily molded as one part, the catch portion having a "horseshoe" shape in cross section. The retraction body can be positioned before the top and bottom portions of the housing body are folded over and joined or it can be pushed through an opening in the back of the housing with the rubber tubing attached. The needle can be fixed in the front of the retraction body after it is positioned inside the housing. These features are well suited to conventional automated molding technology and automated assembly. The few parts and adaptability to automated molding and assembly are features of the invention. Simplicity of design and sureness of operation are also features of the invention.

BRIEF DESCRIPTION OF THE DRAWINGS

FIG. 1 is a plan view of the assembled retractable winged I.V. apparatus in the unretracted position with some interior features shown in dotted outline;

FIG. 2 is a side view of the assembled apparatus of FIG. 1 with some internal features shown in dotted outline;

FIG. 3 is a cut away elevational view of the assembled apparatus along the line 3—3 of FIG. 1;

FIG. 4A is a partially cut away plan view of the unretracted assembly along the lines 4A—4A of FIG. 2 with releasable latch portions on either side in contact with a catch portion near the rear of the retractable body;

FIG. 4B is the same view as FIG. 4A after the releasable latch has been pivoted by means of the projecting portions to release the catch portion of the retraction body which is now free to retract fully;

DETAILED DESCRIPHON OF THE PREFPERRED EMBODIMENT

Figure 6:
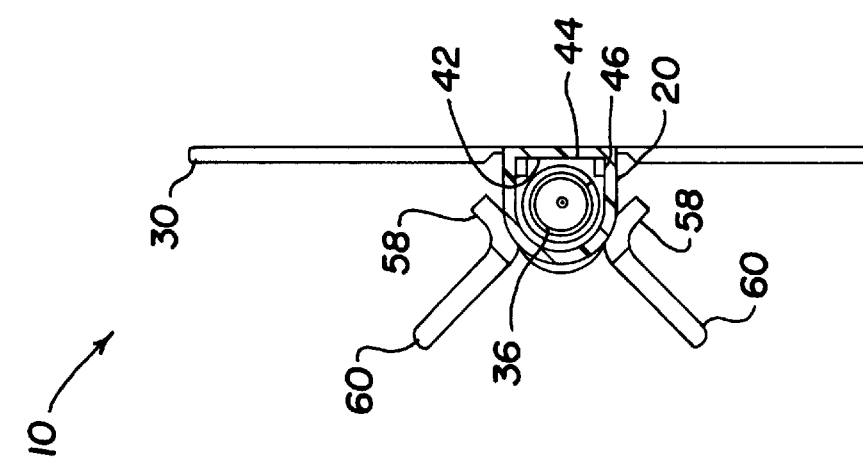
FIG. 6 is an elevation view of the apparatus along the lines 6–6 of FIG. 5 showing the releasable latch in a fully released position.

In FIG. 1, the retractable winged I.V. apparatus is referred to generally by the reference numeral 10. Winged apparatus 10 has an elongated housing 12 having a front end 14 and a back end 18. Elongated housing 12 has an elongated wall 20 and a hollow chamber 22 extending from front end 14 to back end 18. Hollow chamber 22 is divided into a front portion 24 and a rear portion 26 separated by a releasable latch 28.

Wings 30 are attached to wall 20 of body 12 near front 14. Wings 30 are designed to be bendable to some extent to conform to a patient's arm. They are used with tape to hold the I.V. set in place after the vein has been punctured. As will be seen, the apparatus 10 can be retracted without removing the tape or the device from the patient.

A retraction body 32 is mounted for sliding movement within chamber 22. Retraction body 32 is positionable in front portion 24 of the chamber 22 with a hollow needle 34 exposed in front of body 12 for use. A fluid path (not illustrated) extends from the tip of needle 34 through the interior of retraction body 32 so that fluid can pass through it.

Figure 5:
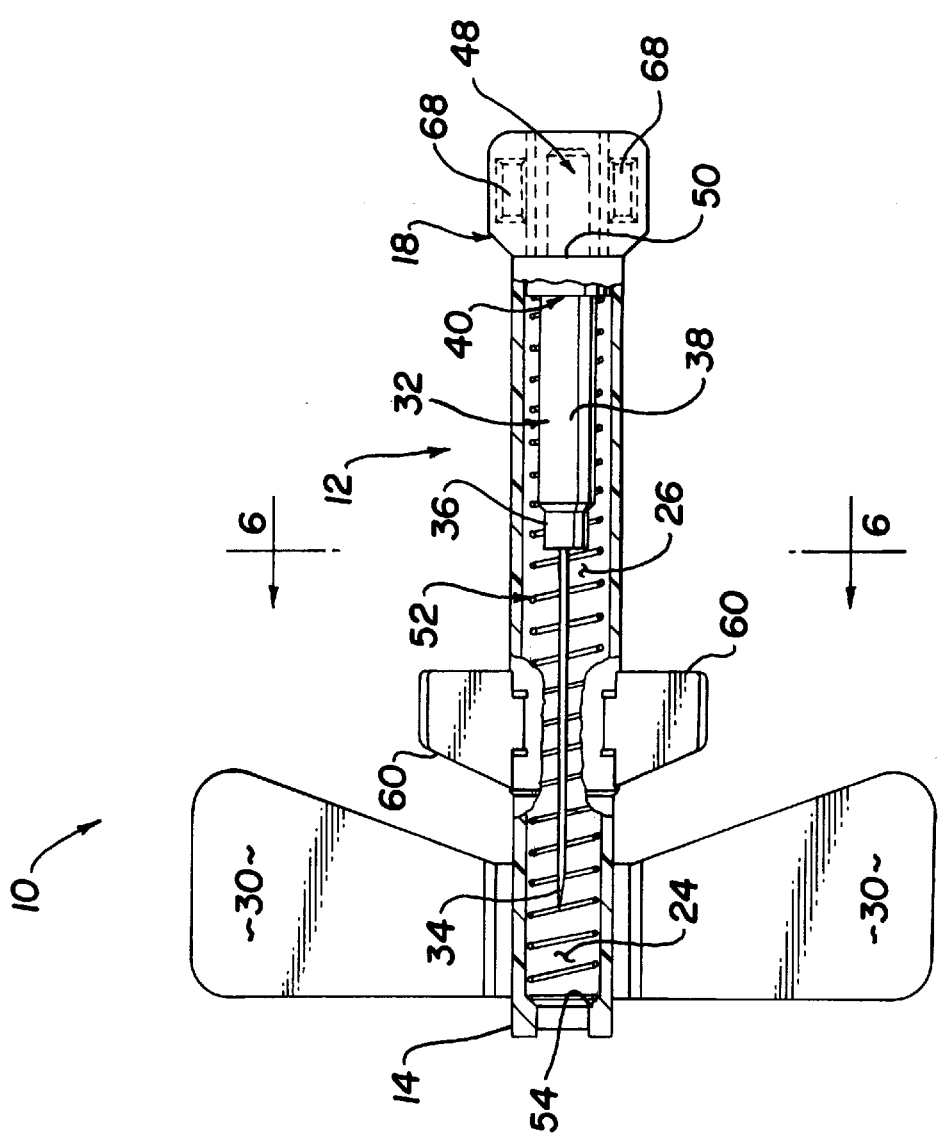
FIG. 5 is a cut away plan view of the retractable winged I.V. apparatus of FIGS. 1–4B showing the retraction body in the fully retracted position with the needle protected.

Best seen in FIGS. 5 and 6, retraction body 32 has a reduced diameter front end portion 36, a main body portion 38 and a catch portion 40 behind main body 38. Portions 36 and 38 are preferably circular, whereas catch portion 40 has a special shape best seen in cross section in FIGS. 3 and 6. It is seen that the wall 20 of housing 12 has a flat surface 42 at its bottom with vertically rising sides which are connected through a rounded top. Portion 40 of 20 the retraction body has a flat surface 44 as its bottom. Surfaces 42, 44 are cooperating surfaces which serve to maintain the orientation of the retraction body relative to the housing while it moves. It should be recognized that different shapes of the retraction body and the housing could be provided with flat or interengaging cooperating surfaces at a location other than the bottom. Surfaces 42, 44 could be located in a different place to maintain relative orientation between the retraction body and the housing. Stops 46 are preferably provided at the rear of the housing to catch the flange on catch portion 40 to prevent it from exiting the body. Stop 46 may be in the form of short slightly inwardly angled ramps that will allow catch portion 40 to pass through during assembly of the retraction body into the chamber. They are exaggerated in the drawings.

A tubing connector 48 extends as a continuation of main body portion 38 from directly behind catch surface 50 on catch portion 40, best seen in FIGS. 4A and 4B. Tubing connector 48 is smaller in diameter than the housing to accommodate a conventional rubber tubing which slips over and covers tubing connector 48, leaving enough clearance with the body to avoid interference with free movement of retraction body 32 as it slides in the housing. Retraction body 32 including tubing connector 48, contain a fluid passageway (not shown) in fluid communication with needle 34 to permit fluids to pass from a fluid container through tubing connected to retraction body 32 and exit from needle 34 into the patient. FIGS. 5 and 6 show retraction body 32 in the flbly retracted position in response to retraction force provided by a biasing element comprising spring 52. Seen in FIG. 5, front 14 has a shelf 54 which provides a seat for the front of spring 52. The back of spring 52 rests against the front 56 of catch portion 40. Spring 52 circumscribes intermediate body portion 38, when compressed.

FIGS. 1–3 show the retractable winged I.V. apparatus in use position with the needle extended from housing 12 and the retraction body positioned in the unretracted condition by means of a releasable latch 27 preferably comprising a pair of generally opposed releasable latches 28. In use position, tubing (not shown) is connected to tubing connector 48 and extends through the body and out the back 18 of the housing. Each releasable latch 28 comprises encroaching part 58 biased to normally encroach into hollow chamber 22 behind catch portion 40 of retraction body 32 to hold retraction body 32 in the unretracted use position of FIG. 1. Latches 28 include projecting parts 60 which serve to pivot encroaching parts 58 into and out of chamber 22 through opposed openings in wall 20. Projecting parts 60 are preferably elevated above the bottom of body 12 and extend laterally away from body 12 so they are conveniently operated jointly by means of the thumb and finger.

Releasable latches 28 are preferably molded into the body 12 for pivoting by means of a living hinge, although they could be a separate part. Each projecting part 60 is generally arranged in right angle relation to it associated encroaching part 58. Releasable latch 27 is configured as dual releasable latches 28 arranged in mirrored relationship to each other on opposite sides of the housing. Although less desirable, releasable latch 27 could comprise but one of the dual configuration since the encroachnent of one encroachable part 58 would be sufficient to contact and restrain surface 50 of catch portion 40 to hold the retraction body in the unretracted condition. Dual latches are provided to increase assurance against premature retraction. Dual latches are especially convenient because the projecting parts can be pinched between thumb and finger, moving from the position of FIG. 4A to the position of FIG. 4B to provide torque free one-handed retraction of the device. This is important because it allows the nurse to hold the patient with one hand while retracting the needle from the patient with the other hand.

In FIG. 4A, encroaching parts 58 may include an angled surface 62. Angled surface 62 may facilitate insertion of retraction body 32 from behind when it is pushed forward to seat catch portion 40 into a seating area 64. From the position of FIG. 4A, all that is necessary for retraction is to squeeze the projecting portions 60 together. This action pivots encroaching parts 58 out of encroachment with the hollow chamber as seen in FIG. 4B to release retraction body 32 for movement to the retracted condition. FIG. 4B shows retraction body 32 completely released and partially retracted. It is moving rearward toward the retracted condition of FIG. 5.

As a matter of preferred construction, front portion 14 of housing 12 has a reduced diameter opening therein designed to comfortably accept front end portion 36 of the retraction body, in the unretracted position. The projecting front portion 36 of body 32 conveniently accepts friction fit protective cap (not shown) over the needle). By reference to FIG. 2, a parting line 66 runs to the front of the housing and represents the place where the two halves of the housing are joined. The housing is preferably laid open in two halves along separation 66 for molding and then folded over to form the housing. Cooperating tabs and openings 68 are provided for mating the two halves together. Back end portion 18 of housing 12 has an opening therethrough into chamber 22. Stops 46 are located in the opening through back end 18 of the housing. They are preferably tapered slightly in the forward direction to facilitate forcing the retraction body through the back end during installation, but which retain the retraction body in the chamber when retracted. The drawings are considerably enlarged, as the body of the retractable winged I.V. apparatus is preferably less than two inches long without the needle. Except for the spring, the parts are preferably molded from polypropylene material commonly used for syringe production.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A retractable IV apparatus, comprising:

an elongated hoensg having a front end, an intermediate portion and a back the housimg having an elongated wall and a hollow chamber extending from the front end to the back end;

the hollow chamber being divided into a front portion and a rear portion separated by an opening in the elongated wall for a releasable latch;

a first pair of wings connected to the housing to attach the structure to a patient, a second pair of wing movably connected to the housing and extending laterally outwardly away from the housing at least one of said second pair of wings comprising a projecting part mounted adjacent said opening and having an encroaching part that privots into and out of said opening in reponse to pivoting movement of said projecting part when the second pair of wings is pinched between a user's fingers, said at least one of said wings comprising a releasable latch for a retraction body;

a needle bearing retraction body mounted for sliding movement within the chamber, the retraction body being positionable in unretracted position in the front portion of the chamber with the needle exposed, the retraction body having a catch portion positionable ahead of the opening to hold the retraction body in the unretracted position with the encroaching part of the at least one second pair of wings of the at least on second pair of wings extended into said opening; and a compressed spring in the front part of the housing mounted in driving contact with the retraction body in its unretracted condition, the string being capable of driving the retraction body into a retacted position in the back of the housing in response to pinching the second pair of wings to move the encroaching part from said opening thereby freeing the retraction body for retraction.

2. The apparatus of claim 1 wherein the retraction body has a back end portion comprising a tubing connector in fluid communication with the needle.

3. The apparatus of claim 2 wherein both the housing and the retraction body are equipped with cooperating surfaces which serve to maintain the orientation of the retraction body relative to the housing.

4. The apparatus of claim 3 wherein the cooperating surfaces are a flat surface in the housing and a flat surface on the retraction body that slides along said flat surface in the housing.

5. The apparatus of claim 4 wherein the flat surface in the housing is a floor of the housing and the flat surface on the retraction body is a flat surface on the bottom of the retraction bodyn which slides along said floor when the retraction body moves.

6. The apparatus of claim 4 wherein the retraction body has a tubing connection which extends behind the catch portion of the retraction body.

7. The apparatus of any one of claims 1–5 wherein the opening in the elongated wall at the intermediate portion of the housing comprises a pair of openings therein and the releasable latch comprises a pair of said releasable latches pivotably mounted in combination with the elongated wall of the housing, for pivotal movement with respect to the housing.

8. The apparatus of claim 7 wherein the at least one of said second pair of wings comgrising a projecting part of said releasable latch is arranged generally in right angle relation to the encroaching part.

9. The apparatus of claim 1 wherein the releasable latch is molded to the wall of the housing by means of a living hinge.

10. A retractable winged IV apparatus, comprising:

an elongated housing havmg a front end, an intermediate portion and a back end, the housing having an elongated wall and a hollow chamber extending from the front end to the back end;

the hollow chamber being divided into a front portion and a rear portion separated by a pair of openings in the elongated wall for receiving releasable latches;

a first pair of wings connected to the housing to attach the structure to a patient;

a second pair of wings movably connected to the housing and extending laterally outwardly away from the housing, each of the second pair of wings comprising a projecting pair mounted adjacent one of the pair of openings and each of the second pair of wings having an encroaching part that pivots into and out of one of the pair of openings in response to pivoting movement of the projecting part when the second pair of wings is pinched between a user's fingers, said second pair of wings comprising dual releasable latches;

a needle beaing retaction body mounted for sliding movement within the chambers the retraction body being positionable in a unretracted position in the front portion of the chamber with the needle exposed, the retraction body having a catch portion positionable ahead of the pair of opcnings to hold the retraction body in the unretracted position with the needle exposed when the encroaching part of the dual releasable latches each are extended into one of the pair of openings;

wherein the retraction body is released for movement to a retracted position within We hollow chamber with the needle being withdrawn into the housing, in response to pinching the second pair of wings to pivot the encroaching parts of the dual releasable latches from the pair of openings thereby free the retraction body for retaction.

11. The apparatis of claim 10 wherein the pair of opening and the dual releasable latches are arranged in mirrored relationship to each other on opposite sides of said housing.

12. The apparatus of claim 11 wherein the projecting parts of said dual releasable latches normaUy extend generally laterally and are elevated with respect to the housings.

13. The apparatus of claim 10 wherein both the housing and the retraction body are equipped with cooperating surfaces which serve to maintain the orientation of the retraction body relative to the housing.

14. The apparatus of claim 13 wherein the cooperating surfaces are a flat surface in the housing and a flat surface on the retraction body that slides along said flat surface in the housing.

15. The apparatus of claim 14 wherein the flat surface in the housing is a floor of the housing and the flat surface on the retraction body is a flat surface on the bottom of the retraction body which slides along said floor when the retraction body moves.

16. The apparatus of claim 10 wherein the retraction body is provided with a catch adapted for contact with thc encroaching parts of the dual releasable latches and a back end portion behind the catch, adapted to make a fluid connection with a fluid transport tube.

17. The apparatus of claim 10 wherein the dual releasable latches are molded to the wall of the housing by means of living hinges.

18. The apparatus of claim 10 wherein said dual releasable latches are biased toward encroachment of the encroaching parts into the hollow chamber.

* * * * *

UNITED STATES PATENT AND TRADEMARK OFFICE
CERTIFICATE OF CORRECTION

PATENT NO. : 6,210,371 B1
DATED : April 3, 2001
INVENTOR(S) : Thomas J. Shaw

It is certified that error appears in the above-identified patent and that said Letters Patent is hereby corrected as shown below:

Column 6, claim 1,
Line 49, delete "hoensg" and insert therefor -- housing --.
Line 50, after back insert -- end, --.
Line 57, after patient insert -- ; --.
Line 58, delete "wing" after pair and insert -- wings --.
Line 60, after ing and before at least insert -- , --.

Column 7, claim 1,
Lines 8 and 9, after pair of wings delete "of the at least on second pair of wings" before extended into.
Line 9, add a paragraph break after and.
Line 12, delete "string" and insert -- spring --.

Column 7, claim 5,
Line 32, delete "bodyn" and insert -- body --.

Column 7, claim 8,
Line 45, delete "comgrising" and insert -- comprising.

Column 7, claim 10,
Line 58, after wall insert -- , --.

Column 8, claim 10,
Line 4, delete "pair" and insert -- part --.
Line 12, delete "beaing" and insert -- bearing --.
Line 13, delete "chambers" and insert -- chamber, --.
Line 14, delete "a" and insert -- an --.
Line 17, delete "opcnings" and insert -- opening --.
Line 22, delete "We" and insert -- the --.
Line 27, delete "free" and insert -- freeing --.
Line 28, delete "retaction" and insert -- retraction .

UNITED STATES PATENT AND TRADEMARK OFFICE
CERTIFICATE OF CORRECTION

PATENT NO. : 6,210,371 B1
DATED : April 3, 2001
INVENTOR(S) : Thomas J. Shaw

It is certified that error appears in the above-identified patent and that said Letters Patent is hereby corrected as shown below:

Column 8, claim 11,
Line 29, delete "opening" and insert -- openings --.

Column 8, claim 12,
Line 33, delete "normaUy" and insert -- normally --.
Line 34, delete "housings" and insert -- housing --.

Column 8, claim 16,
Line 49, delete "thc" and insert -- the --.

Signed and Sealed this

Sixth Day of November, 2001

Attest:

*Nicholas P. Godici*

NICHOLAS P. GODICI
*Attesting Officer*  *Acting Director of the United States Patent and Trademark Office*